(12) United States Patent
Enk

(10) Patent No.: US 9,162,033 B2
(45) Date of Patent: Oct. 20, 2015

(54) DILATOR FOR PERFORMING A PERCUTANEOUS MEDICAL PROCEDURE

(75) Inventor: Dietmar Enk, Coesfeld (DE)

(73) Assignee: Cook Medical Technologies LLC, Bloomington, IN (US)

( * ) Notice: Subject to any disclaimer, the term of this patent is extended or adjusted under 35 U.S.C. 154(b) by 1834 days.

(21) Appl. No.: 11/993,921

(22) PCT Filed: Jun. 27, 2005

(86) PCT No.: PCT/DK2005/000429
§ 371 (c)(1),
(2), (4) Date: Jun. 3, 2008

(87) PCT Pub. No.: WO2007/000159
PCT Pub. Date: Jan. 4, 2007

(65) Prior Publication Data
US 2009/0199849 A1    Aug. 13, 2009

(51) Int. Cl.
*A61F 11/00* (2006.01)
*A61M 16/04* (2006.01)
*A61M 29/00* (2006.01)

(52) U.S. Cl.
CPC ....... *A61M 16/0465* (2013.01); *A61M 16/0472* (2013.01); *A61M 29/00* (2013.01); *A61M 2210/1032* (2013.01)

(58) Field of Classification Search
CPC ... A61F 2/95; A61F 2/958; A61F 2002/9517; A61B 2017/1205; A61B 17/12022; A61B 17/12145; A61B 17/1215; A61B 17/3417; A61B 17/3462; A61B 1/31; A61M 29/00; A61M 2025/1088; A61M 2025/1093; A61M 2205/0222; A61M 2205/0238; A61M 2025/0687; A61M 16/0465–16/0488; A61M 2029/025; A61M 25/0068; A61M 25/0045; A61M 2025/0046; A61M 2025/0056–2025/0057; A61M 2025/006; A61M 2025/00; A61M 2025/0062; A61M 2210/1032; B29C 43/10; B29C 46/10; A61J 15/0015; A61J 15/0026; A61J 15/0023
USPC .............. 606/190–198; 128/200.26; 604/264; 600/184
See application file for complete search history.

(56) References Cited

U.S. PATENT DOCUMENTS

| | | | | |
|---|---|---|---|---|
| 3,788,326 A | * | 1/1974 | Jacobs | 128/207.15 |
| 3,809,091 A | * | 5/1974 | Shute | 606/119 |
| 4,211,234 A | * | 7/1980 | Fisher | 128/200.26 |
| 4,236,520 A | * | 12/1980 | Anderson | 604/264 |
| 4,402,684 A | * | 9/1983 | Jessup | 604/264 |
| 4,535,759 A | * | 8/1985 | Polk et al. | 601/2 |
| 4,762,130 A | * | 8/1988 | Fogarty et al. | 606/159 |
| 4,852,565 A | * | 8/1989 | Eisele | 128/207.14 |
| 4,955,859 A | * | 9/1990 | Zilber | 604/8 |

(Continued)

FOREIGN PATENT DOCUMENTS

| | | | | |
|---|---|---|---|---|
| EP | 1 415 679 A1 | | 5/2004 | ........... A61M 16/04 |
| WO | WO 93/24170 A | | 12/1993 | ........... A61M 16/04 |
| WO | WO 02066095 | * | 8/2002 | |

*Primary Examiner* — Amy R Weisberg
(74) *Attorney, Agent, or Firm* — Brinks Gilson & Lione

(57) ABSTRACT

A dilator (100) for performing a percutaneous medical procedure, said dilator (100) comprising a proximal shaft portion (112) near a proximal end (114) thereof and a distal portion having a general tapering shape towards a distal end (120) of said dilator (100), said distal portion being adapted for dilation of body tissue.
To provide a dilator which can shorten time of procedure a region of an outer surface of said distal portion is provided with a pattern of depressions having a depth in the interval of 0.1 to 3 mm.

20 Claims, 3 Drawing Sheets

(56) References Cited

U.S. PATENT DOCUMENTS

Figure 1:
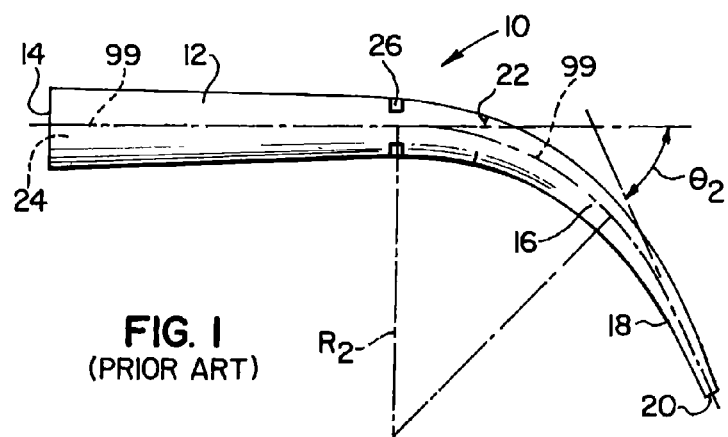

| | | | |
|---|---|---|---|
| 5,056,515 A * | 10/1991 | Abel | 128/207.15 |
| 5,217,005 A * | 6/1993 | Weinstein | 128/200.26 |
| 5,244,619 A * | 9/1993 | Burnham | 264/171.2 |
| 5,339,809 A * | 8/1994 | Beck et al. | 128/207.29 |
| 5,397,302 A * | 3/1995 | Weaver et al. | 604/93.01 |
| 5,423,745 A * | 6/1995 | Todd et al. | 604/500 |
| 5,496,292 A * | 3/1996 | Burnham | 604/526 |
| 5,509,899 A * | 4/1996 | Fan et al. | 604/103.14 |
| 5,709,874 A * | 1/1998 | Hanson et al. | 424/423 |
| 6,214,030 B1 * | 4/2001 | Matsutani et al. | 606/223 |
| 6,245,045 B1 * | 6/2001 | Stratienko | 604/164.13 |
| 6,286,509 B1 * | 9/2001 | Nash et al. | 128/207.14 |
| 6,524,275 B1 * | 2/2003 | Lynch et al. | 604/96.01 |
| 6,595,959 B1 * | 7/2003 | Stratienko | 604/164.13 |
| 6,637,435 B2 | 10/2003 | Ciaglia et al. | 128/207.29 |
| 6,942,681 B2 * | 9/2005 | Johnson | 606/194 |
| 7,572,270 B2 * | 8/2009 | Johnson | 606/194 |
| 2002/0066453 A1 * | 6/2002 | Ciaglia et al. | 128/207.29 |
| 2002/0077655 A1 | 6/2002 | Frova | 606/196 |
| 2005/0267448 A1 * | 12/2005 | Bonnet et al. | 606/1 |
| 2013/0025588 A1 * | 1/2013 | Bosel | 128/200.26 |

* cited by examiner

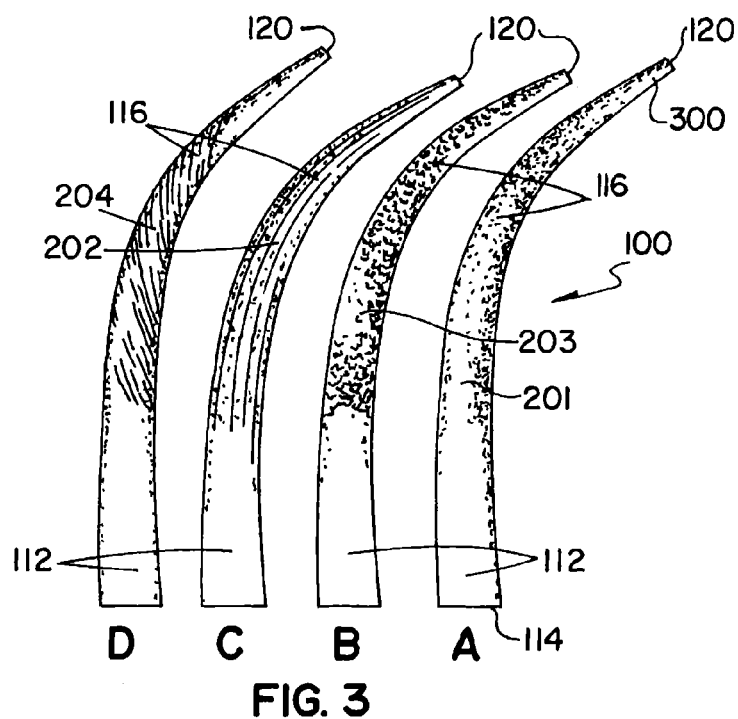
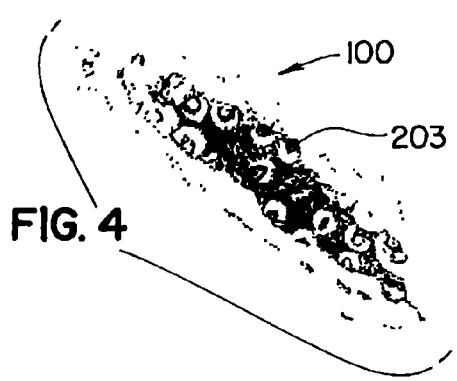
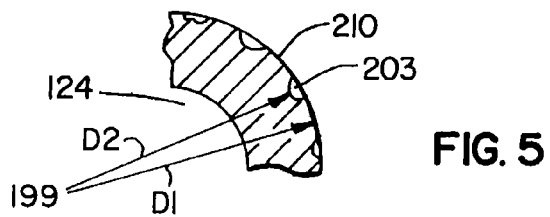

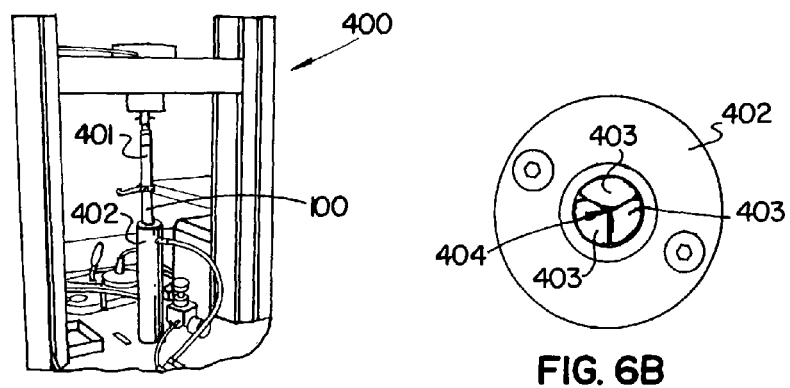
FIG. 6A
FIG. 6B
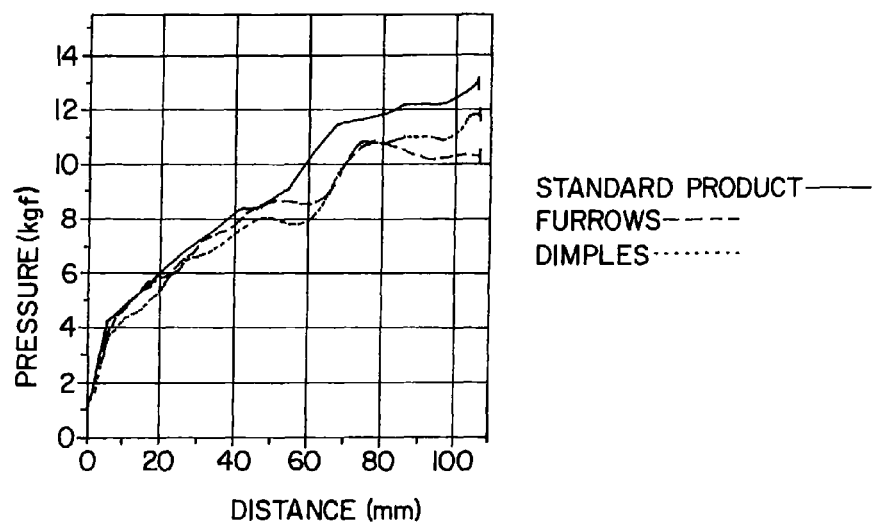
STANDARD PRODUCT ——
FURROWS - - - -
DIMPLES ·········
FIG. 7

DILATOR FOR PERFORMING A PERCUTANEOUS MEDICAL PROCEDURE

This application is the national phase under 35 U.S.C. §371 of PCT International Application No. PCT/DK2005/000429, which has an International filing date of 27 Jun. 2005, which designated the United States of America and is incorporated herein by reference in its entirety.

The present invention relates to a dilator for performing a percutaneous medical procedure, said dilator comprising a proximal shaft portion near a proximal end thereof and a distal portion having a general tapering shape towards a distal end of said dilator, said distal portion being adapted for dilation of body tissue.

In critical care of a seriously ill or injured patient, the first step is establishment of an adequate air passageway to maintain the ability of the patient to breathe, or to perform resuscitation on a patient unable to breathe. Endotracheal intubation (placement of a tube through the nostrils or mouth and into the trachea) is the preferred method, but it is not always possible e.g. because of obstruction of the nostrils and/or mouth or because of secretions. The most direct way to provide an air passageway under these circumstances is to form an opening (stoma) in the tracheal wall, and to keep the stoma open by inserting a tracheal tube into it. Such tracheostomy is a common procedure performed on critically ill persons to facilitate long-term airway management. In a surgical tracheostomy, one or more tracheal rings are cut with a scalpel to provide an opening of sufficient size for the tracheal tube to be inserted. This procedure often entails a high degree of surgical skill to perform, particularly since it is vital to locate and avoid unintentional severing of the blood vessels in the area. Further the cost is relatively high as it is necessary to carry out the procedure in an operating room. In recent years so-called percutaneous tracheostomy procedure has found widespread use, as it is a minimal invasive procedure having fewer complications and resulting in a more cosmetic scar compared to surgical procedures, and further percutaneous tracheostomy can be performed as a bedside procedure, obviating the need for an operating room. In percutaneous tracheostomy only a small opening is incised as an entrance, and thereafter the opening is gradually enlarged with a dilator. By this percutaneous tracheostomy a stoma between the tracheal rings can be formed, resulting in reduced blood loss compared to the surgical tracheostomy in which one or more tracheal rings are cut. Percutaneous tracheostomies can be formed in various ways. One technique involves the steps of inserting a hollow needle through the skin into the trachea, inserting a guidewire in the needle, withdrawing the needle over the guidewire and then using one or more dilators slid over the guidewire to expand the opening sufficiently to enable a tracheostomy tube to be inserted. Where a series of several dilators is used these have an increasing diameter so that the opening is gradually expanded. As an alternative a single, more steeply tapered dilator can be used, such as the well-known Cook® Ciaglia Blue Rhino™ dilator, which is described in U.S. Pat. No. 6,637,435. This dilator of the related art is a dilator for creating a tracheostomy in one pass. The dilator comprises a generally linear shaft extending from a proximal end and a gradually and continuously curved distal portion with continuously decreasing diameter (from about 38 French) to a distal tip portion of small diameter of about 12 French at the distal end.

EP 1 415 679 A1 discloses another tracheostomy dilator moulded from a plastics material and formed into an S-shape having a flexible, tapered distal end for insertion into trachea.

DE 100 65 604 A1 also relates to a tracheostomy dilator comprising a shaft portion or hand grip and a conical dilator portion.

The use of a single dilator is an advantage because it reduces the number of steps in the procedure and the number of components. One drawback associated with this technique is that it can require some force to insert the dilator and this insertion requires a certain degree of skill and care to avoid trauma to the patient, such as collapse of trachea or damage to the posterior tracheal wall, for which reason the time of procedure is relatively long.

It is an object of the present invention to provide a dilator, which can shorten time of procedure.

To achieve this object, the dilator indicated in the introduction is characterized in that a region of an outer surface of said distal portion is provided with a pattern of depressions having a depth in the interval of 0.1 to 3 mm. It is found that by providing such depressions, the force required to introduce the dilator is reduced compared to a conventional prior art dilator having a smooth outer surface. As the force required to introduce the dilator is reduced, the risk of trauma is reduced and the requirement of care during the procedure is less strict, meaning the procedure can be performed in shorter time. Although values exceeding 3 mm may be used, the wall thickness of the dilator will often be limited, particularly it the dilator is hollow, and this restricts the higher limit of the interval. A value below 0.1 mm is generally too small to achieve a measurable effect.

According to an embodiment, the distance between adjacent depressions is in the interval of 0.1 to 5 mm, which is found to provide good results.

The area of the depressions in relation to the surface area influence the force necessary to urge the dilator into a stoma, and according to an embodiment, the depressions constitute 1-98% of the surface area in said region.

The depressions may be distributed only partly around the distal portion, however according to an embodiment depressions are distributed around the distal portion along a substantial portion thereof, such as at least 50% of the length of the distal portion, such as 80%, although acceptable results may be achieved with less than 50%, such as 25%, particularly if the depressions are distributed at carefully selected regions, such as at the widest dilation, i.e. near the shaft portion.

According to an embodiment, the depressions are distributed in a random pattern. Dependent on the method of manufacture, a random pattern may be cost saving.

In an alternative embodiment, the depressions are distributed in a regular pattern. By carefully distributing the depressions in a regular pattern, favourable results may be achieved.

According to an embodiment, the depressions are formed in the surface as indentations, grooves, furrows, dimples, texture, grinding marks or the like. This kind of depressions provides relatively smooth depressions, so the risk of unintentional damage to the tissue by the dilator is limited. It is generally relatively easy to provide grinding marks in the surface, and hence grinding marks as depressions may be cost effective regarding manufacture. However grinding marks are less appropriate than the other types of depressions as grinding marks often will not have the necessary depth.

The depressions may be distributed randomly on the surface of the dilator. In case of grooves or furrows, it may be advantageous that said grooves or furrows are oriented in a direction along the dilator from end to end.

Alternatively, said grooves or furrows may be oriented in a circumferential direction of the dilator.

In yet another alternative embodiment, said grooves or furrows are oriented along helical paths. Hereby a certain degree of screw effect may be achieved. This screw effect may be advantageous in some procedures to facilitate insertion of the dilator.

In a further alternative embodiment, said grooves or furrows are oriented along crossing helical paths, an angle α between two crossing helical paths being in the interval of 60-120°.

The dilator may be made of any suitable material, such as a metal, but according to an embodiment, the dilator is manufactured from a polymer, which is found to provide very cost-effective dilators. Hence the dilator may be disposable, eliminating the need for cleaning of the dilator and the risk of cross-infection.

To further reduce the friction, and hence reduce the force necessary to urge the dilator into a stoma, the distal portion of the dilator may be provided with a hydrophilic coating.

According to an embodiment, the dilator is adapted to be advanced over a guidewire, to thereby facilitate entry of the dilator, and reduce the risk of damages to the patient.

Further providing the dilator with an inflatable balloon at a distal portion of the dilator may be advantageous. The balloon may be inflated to provide an increased dilation, or to facilitate a careful, controlled dilation.

An embodiment of the invention relates to a device for forming an ostomy in a tracheal wall, said device comprising a dilator according to any of the claims above, wherein the device further comprises a reinforced balloon catheter carried by said dilator, the balloon catheter including an inflatable balloon extending from the distal end of the dilator, said dilator and balloon catheter being advanceable along a guide wire percutaneously positionable across the tracheal wall, said balloon being adapted to atraumatically dilate a portion of the tracheal wall to form an ostomy in the tracheal wall upon inflation of the balloon. By this device the risk of injury to the trachea and especially the posterior tracheal wall is reduced.

Another aspect of the invention relates to a method for making a dilator having a surface as outlined above, comprising the steps of:
providing a dilator in a suitable biocompatible material, such as a polymer, by either pressure die-casting in a mould having a surface with a pattern complementary to the pattern to be achieved on the dilator, or by machining the smooth surface of a dilator blank to provide a dilator having a pattern of depressions on the outer surface thereof. It may also be possible to produce the dilator by extrusion.

Yet another aspect of the invention relates to a percutaneous method of forming an ostomy in a tracheal wall employing a dilator comprising a proximal shaft portion near a proximal end thereof and a distal portion having a general tapering shape towards a distal end of said dilator, said distal portion being adapted for dilation of body tissue, a region of an outer surface of said distal portion being provided with a pattern of depressions, the method comprising the steps of:
percutaneously inserting the tip of a guide wire through the tracheal wall so that the guide wire lies across the tracheal wall,
positioning the dilator over the guide wire,
advancing the dilator along the guide wire until the dilator lies across the tracheal wall.

By this method a fast and essentially atraumatic dilation of an ostomy may be performed.

Figure 2:
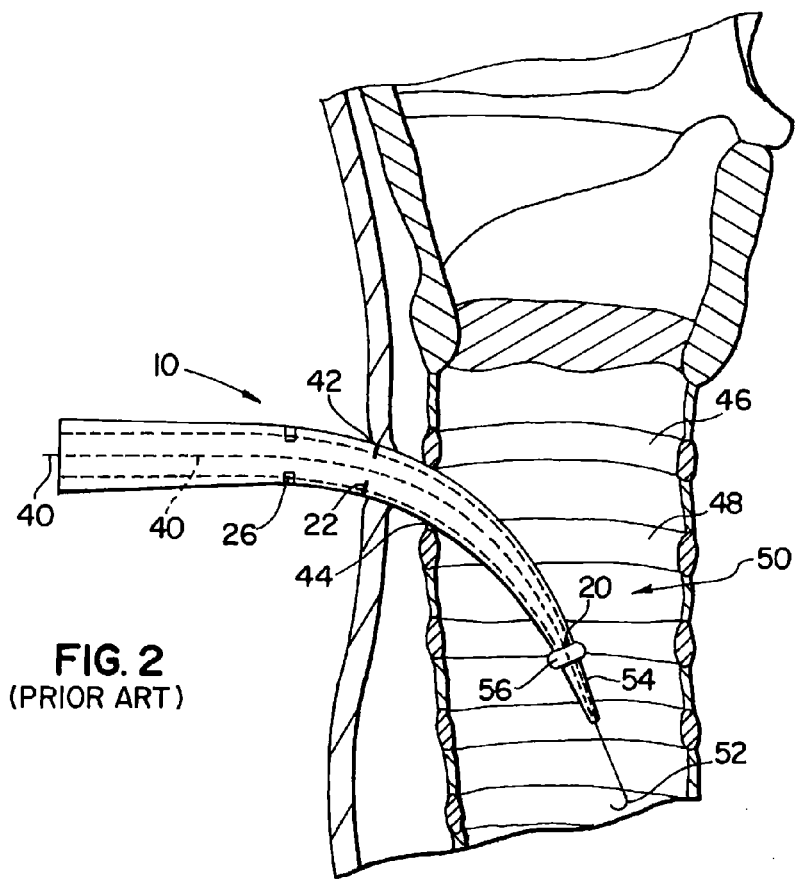

In the following the present invention will be described in more detail, by way of example, with reference to the accompanying drawing, in which:

FIG. 1 is a side view of a prior art dilator,
FIG. 2 is a side view of the dilator of FIG. 1 in position over a guidewire and extending through an entrance to a trachea,
FIG. 3 is a side view of four dilators a-d according to the invention,
FIG. 4 is an enlargement of a surface portion of dilator b in FIG. 3,
FIG. 5 is a sketch of a partial cross-section of a dilator according to the invention,
FIG. 6a is a view of a test set-up,
FIG. 6b is an enlarged view of a part of the set-up of FIG. 6a, and
FIG. 7 is a curve showing force versus distance.

A prior art dilator 10 of U.S. Pat. No. 6,637,435 is illustrated in FIG. 1. The dilator according to the present invention may be seen as a further development of this prior art dilator, and the following description of the prior art dilator is valid for the dilator according to the invention as well. The dilator 10 includes a shaft portion 12 extending from a proximal end 14, and a curved tapered distal portion 16 extending from shaft portion 12 to a small tip portion 18 at distal end 20. A centre line 99 extends through the dilator 10 from the proximal end 14 to the distal end 20. Demarcation 22 denotes the location at which the outer diameter is 38 French (12.7 mm). A central passageway 24 extends completely there through from proximal end 14 to distal end 20. A marking 26 is identified toward proximal end 14 from demarcation 22 that indicates the recommended depth of maximum insertion into the thorax, and that is at that location at which the shaft portion 12 and the curved tapered distal portion 16 meet.

Preferred dimensions of dilator 10 for use especially in tracheostomy procedures are: an overall length of about 196 to 210 mm (7.75 to 8.25 in); a length of about 110 mm (4.33 in) from distal end 18 to insertion depth marking 26; an inner diameter at distal end 20 of about 2.79 mm (0.110 in) and that extends the short length of flexible tip portion 18, about 3.18 mm (0.125 in); an outer diameter at distal end 18 of about 12 French or 4 mm (0.140 in); and an outer diameter at proximal end 14 of about 50 French or 16.5 mm (0.650 in), with an inner diameter of about 12.0 mm (0.473 in). The outer diameter at demarcation 22, as mentioned above, is about 38 French or 12.7 mm (0.491 in) and is located at about a distance of 80 mm (3.150 in) from distal end 20; and the inner diameter at demarcation 22 is about 7.72 mm (0.304 in).

The taper of the curved tapered distal portion 16 of the example described is about 0.056 mm per mm, or 3.19°. The taper may be within a range of tapers of between 1.70 and 10°. A very gradual taper such as about 1°00' may also, if desired, be used for the shaft portion 12 for facilitating removal of the moulded dilator from the moulding apparatus. Continuation of the taper in the proximal direction from curved tapered distal portion 16 also serves to permit, if necessary, further widening of the ostomy beyond 38 French, such as to 40.5 French at the insertion limit 26.

The curvature of curved tapered distal portion 16 may be a series of curves of different radii, or a complex curve, from distal end 20 at least to demarcation 22. The portion of dilator 10 between demarcation 22 and insertion limit 26 will extend, during use of the dilator, between the outer skin of the patient and the inside or anterior surface of the trachea of the patient. Also, the optimum curvature may be within a range such that the outer surfaces are within a zone of tolerance. While not susceptible of a precise mathematic definition, it is preferred that the curvature be adapted to the curvature of conventional curved tracheostomy tubes.

The curved distal portion 16 constitutes a gradual transition from a very flexible short tip portion 18 at distal end 20, to a more rigid shaft 12 at insertion limit 26, thus having increasing rigidity in the direction extending away from distal end 20. Such flexibility transition may be generated such as providing a very small wall thickness at distal end 18 (e.g., 0.381 mm or 0.015 in) and greater wall thickness along shaft 12 of about 2.49 mm (0.098 in). Shaft 12 may also have a gradual taper, if desired. Dilator 10 may be made from polyurethane and be of softer durometer than prior art dilators, such as a durometer of about 43 Shore D hardness. Fabrication may be accomplished such as by moulding the dilator initially in a linear tapered shape with appropriate wall thicknesses, and then inserting through the central passageway a rigid forming wire of stainless steel having an appropriate curved shape to elastically deform the dilator from its initial linear shape to generate the desired curve of the intermediate portion, and then post-curing the dilator at elevated temperatures with the forming wire in place, after which the dilator retains an appropriately curved shape. Sharp edges at the proximal end may be removed by abrasion, and the edges of the tip at distal end 20 may be rounded by careful application of localized heating and pressure to remove sharp edges.

Dilator 10 may have a hydrophilic coating along curved tapered end portion 16 such as PHOTO-LINK coating material commercially available from SurModics, Inc., Eden Prairie, Minn. The material is a liquid mixture of PV05 Photo-Polyvinylpyrrolidone copolymer, PA05 Photo-Polyacrylamide copolymer, 2-propanol and distilled water. Upon the intermediate and distal end portions of the dilator being dipped into a bath of the mixture, with the distal end being occluded to isolate the interior surfaces, the coating on the dilator is cured by ultraviolet light at 150 wpi. Dilator 10 is preferably of radiopaque material, and it may be blue in colour to minimize glare when viewed by an endrotracheal bronchoscope that is in position in the patient above the tracheal ring 46 to view the procedure within the trachea from above the tracheal entrance.

FIG. 2 illustrates the use of dilator 10 positioned on and along a guidewire 40 that extends through incision 42 of a patient and in tracheal entrance 44 between adjacent tracheal rings 46, 48, to introduce a tracheostomy tube (not shown) into trachea 50. Guidewire 40 includes a flexible J-shaped tip 52 and a guiding catheter 54 of 8.0 French over much of the guidewire. Guiding catheter 54 preferably includes an annular protrusion 56 there around to act as a stop for the distal end 20 of dilator 10. Dilator 10 is inserted over guidewire 40 until distal end 20 abuts annular protrusion 56. As can be seen in FIG. 2, the guidewire 40 is directed downwards into the trachea to avoid that the dilator 10 abuts the posterior tracheal wall to avoid injury thereof.

With the curved tapered distal portion 16 hydrated such as by being dipped into sterile saline or water to hydrate and thus activate the hydrophilic coating thereon, dilator 10 is moved along guiding catheter 54 and the distal tip portion of dilator 10 is inserted into tracheal entrance opening. The assembly is then gently urged repeatedly into and partially withdrawn from the tracheal entrance opening 44 and prying apart tracheal rings 46, 48 in an iterative procedure, increasing the insertion depth gradually each time until tracheal entrance opening 44 has been made sufficiently wide to enable a tracheostomy tube of appropriate size to be inserted there through. Once hydrated by being immersed into sterile saline or water, the outer surface of curved tapered distal portion is made slippery without the use of lubricating jelly, with a lowered coefficient of friction to minimize trauma to the patient. Marking 26 indicates the safety limit of insertion of the dilator into the patient's incision 42.

Dilator 10 is then removed from guidewire 40, and a loading dilator (not shown) of appropriate size is placed thereon, with the tracheostomy tube already placed on the loading dilator, extending through the widened tracheal entrance opening.

Four dilators according to the present invention can be seen in FIG. 3. As can be seen, the general outline of the dilators is similar to the prior art dilator 10 in FIGS. 1 and 2. The dilators 100 comprise a proximal shaft portion 112 near a proximal end 114 of the dilator. The dilators 100 further comprise a tapered and curved distal portion 116 extending from a position at or near a distal end 120. A region of an outer surface of the distal portion 116 is provided with depressions, such as illustrated in FIG. 3*a-d*. In FIG. 3*a*, the depressions are grinding marks 201, in FIG. 3*b* dimples 203, in FIG. 3*c* grooves 202, and in FIG. 3*d* furrows 204. The pattern of depressions may be provided as any regular or irregular distribution of depressions on the surface. The depressions may be provided by machining, or by providing a suitable mould having a non-smooth, e.g. textured, surface in case of a moulded dilator. The pattern of depressions is an important difference to the prior art as illustrated in FIGS. 1 and 2, as the outer surface of the distal portion 16 of the prior art dilator 10 described above is smooth. In the embodiment shown, the dilators 100 have a smooth region 300 at the distal end 120 thereof, mainly because the wall thickness is relatively small at this part of the dilator. Further the dilation performed by the dilator at this region is limited. As can be seen, the furrows 204 of dilator 100 in FIG. 3*d* are helical or twisted, whereby a screw effect can be achieved, which may facilitate in the insertion and dilation. Each furrow 204 may extend continuously from the distal end 120 to the proximal shaft portion 112, or alternatively or supplementary the furrows 204 may be discontinued to extend for only a limited part of the total distance from the distal end 120 to the proximal shaft portion 112. Similarly the grooves 202 of the dilator of FIG. 3*c* may extend continuously from the distal end 120 to the proximal shaft portion 112, or alternatively or supplementary the grooves 202 may be discontinued to extend for only a limited part of the total distance from the distal end 120 to the proximal shaft portion 112.

An enlarged view of a portion of the surface of the dilator 100 in FIG. 3*b* can be seen in FIG. 4. As can be seen the surface of the dilator 100 is provided with randomly distributed depressions in the form of pitting or dimples 203.

A simplified sketch of a partial cross-section of the dilator 100 of FIG. 4 can be seen in FIG. 5, which is solely for illustration of the principle of the depressions of the surface of the dilator 100. The dimples 203 provide a depression or relief area at a second distance D2 from a centre line 199 through the dilator from a proximal end 114 to a distal end 120. On the other hand, the unpitted part of the outer surface 210 provides a projection or contact area at a first distance D1. The difference between D1 and D2 may be denoted the depth of the depressions and is a measure of the surface irregularity or roughness, and is found to influence the force necessary to urge a dilator into trachea of a patient. In FIG. 5, a central passageway 124 extending through the dilator can also be seen. This passageway 124 can be used for the dilator 100 to be slid along a guidewire, similar to the illustration in FIG. 2.

A test set-up 400 for measuring the force necessary to urge a dilator 100 into a narrow opening in a yielding channel can be seen in FIG. 6*a*. In the test, the dilator 100 was straightened out and mounted in a holder 401. The dilator 100 was then urged into a channel of a simulator part 402, which can be seen in more detail in FIG. 6*b*, which is a top view of the simulator part 402 seen from the side in FIG. 6*a*. The simulator part 402 is a simulation of the trachea wall. Inside the simulator part 402 three inflatable balloon members 403 are arranged. When the balloon members 403 are inflated as illustrated in FIG. 6b, they fill the channel in the simulator part 402 leaving only a narrow opening 404 between the balloon members 403.

The force required to urge the different dilators 100 into the simulator part 402 was recorded and the resulting graphs can be seen in FIG. 7. The temperature at the test was 23.8° C., the humidity 24.2%, and the speed was 254 mm/minute. As can be seen the maximum force necessary to press the standard prior art dilator having a smooth surface into the simulator is significantly higher than the maximum force necessary with dilators having a surface provided with dimples or furrows. The maximum force required is reduced by approximately 10% by the dilator having dimples, whereas a reduction of approximately 23% is achieved by the dilator having furrows in the surface.

Although the examples given relates to depressions of relatively limited dimensions, it will be evident to the skilled person that protrusions, such as fins, corresponding to depressions of relatively large dimensions, will also be a possibility.

Although the present invention is described in relation to a dilator for tracheostomy, it is also beneficial in relation to other dilators, such as cervical dilators as will be appreciated by the skilled person. The dilator may also be used for providing access through the chest of a patient for example at the ribs, e.g. for access directly to the lungs for connection to a respirator or for drainage of fluid in the lungs.

The invention claimed is:

1. A dilator for performing a percutaneous medical procedure, said dilator comprising a proximal shaft portion near a proximal end thereof, a curved tapered distal portion with a wall having a preset curved shape and a tapered outer surface extending toward a distal end thereof, and an interior passageway extending completely therethrough, a guidewire thereby being extendable through said interior passageway, said interior passageway defined by said wall having a wall thickness, said wall thickness extending between said interior passageway and said tapered outer surface of said wall, said curved tapered distal portion being adapted to enlarge a stoma by urging the curved tapered distal portion into said stoma, and said preset curved shape being molded from a polymer to retain said preset curved shape, wherein a region of said tapered outer surface of said curved tapered distal portion is provided with a pattern of depressions extending radially into said wall from said region of said tapered outer surface partially toward said interior passageway to a depth of 0.1 to 3 mm, said pattern of depressions reducing a force required to urge said curved tapered distal portion into said stoma.

2. A dilator according to claim 1, wherein a distance between adjacent depressions is in an interval of 0.1 to 5 mm.

3. A dilator according to claim 1, wherein the depressions constitute 1-98% of a surface area in said region of said tapered outer surface.

4. A dilator according to claim 1, wherein said depressions are distributed around the curved tapered distal portion along a substantial portion thereof.

5. A dilator according to claim 4, wherein said depressions are distributed along about 80% of a length of said curved tapered distal portion.

6. A dilator according to claim 4, wherein said depressions are distributed along at least about 50% of a length of said curved tapered distal portion.

7. A dilator according to claim 1, wherein the depressions are distributed in a random pattern.

8. A dilator according to claim 1, wherein the depressions are distributed in a regular pattern.

9. A dilator according to claim 1, wherein depressions are formed in the tapered outer surface as indentations, grooves, furrows, dimples, texture or grinding marks.

10. A dilator according to claim 9, wherein said grooves or furrows are oriented in a direction along the dilator from the proximal end to the distal end.

11. A dilator according to claim 9, wherein said grooves or furrows are oriented in a circumferential direction of the dilator.

12. A dilator according to claim 9, wherein said grooves or furrows are oriented along helical paths.

13. A dilator according to claim 1, wherein said dilator is manufactured from a polymer.

14. A dilator according to claim 1, wherein said curved tapered distal portion is provided with a hydrophilic coating.

15. A dilator according to claim 1, said dilator being adapted to be advanced along the guidewire.

16. A dilator for performing a percutaneous medical procedure, comprising:
a member extending from a proximal end to a distal end with a passageway extending completely therethrough defined by a wall, a guidewire thereby being extendable through said passageway and said wall extending between said passageway and a tapered outer surface thereof, the member having a proximal shaft portion and a curved distal portion with said wall having a preset curved shape, said tapered outer surface having a gradual taper in a direction of said distal end, said tapered outer surface being adapted to enlarge a stoma by urging the tapered outer surface into said stoma, and said preset curved shape being molded from a polymer to retain said preset curved shape, wherein a region of said tapered outer surface of said curved distal portion is provided with a pattern of depressions extending radially partially into said wall from said region of said tapered outer surface, said pattern of depressions reducing a force required to urge said tapered outer surface into said stoma.

17. A dilator according to claim 16, wherein the depressions constitute 1-98% of a surface area in said region of said tapered outer surface.

18. A dilator according to claim 16, wherein said depressions are formed in the surface as indentations, grooves, furrows, dimples, texture or grinding marks.

19. A dilator according to claim 16, wherein said depressions extend radially into said wall to a depth of 0.1 to 3 mm.

20. A dilator according to claim 16, wherein said depressions are distributed along at least about 50% of a length of the curved distal portion.

* * * * *